(12) United States Patent
Omura et al.

(10) Patent No.: US 6,608,185 B1
(45) Date of Patent: *Aug. 19, 2003

(54) SUBSTANCES KF-1040T4A, KF-1040T4B, KF-1040T5A, AND KF-1040T5B, AND PROCESS FOR PRODUCING SAME

(75) Inventors: Satoshi Omura, Tokyo (JP); Hiroshi Tomoda, Tokyo (JP); Rokuro Masuma, Tokyo (JP)

(73) Assignee: Kitasato Institute, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/937,335

(22) PCT Filed: Mar. 25, 1999

(86) PCT No.: PCT/JP99/01526

§ 371 (c)(1), (2), (4) Date: Jan. 14, 2002

(87) PCT Pub. No.: WO00/58491

PCT Pub. Date: Oct. 5, 2000

(51) Int. Cl.[7] .......................... C07H 15/00; C12P 19/44; C12N 1/00; A61K 31/70
(52) U.S. Cl. .......................... 536/4.1; 435/74; 435/822; 514/25
(58) Field of Search .......................... 514/25; 536/4.1; 435/74, 822

(56) References Cited

U.S. PATENT DOCUMENTS 6,350,604 B1 * 2/2002 Hirayama et al. .......... 435/198
6,432,682 B1 * 8/2002 Omura et al. .............. 435/74

* cited by examiner

Primary Examiner—James O. Wilson
Assistant Examiner—Ganapathy Krishnan
(74) Attorney, Agent, or Firm—Young & Thompson

(57) ABSTRACT

A microorganism which belongs to the genus Gliocladium and has the ability to produce stereoisomers KF-1040T4A and KF-1040T4B which are compounds represented by the following formula [I],

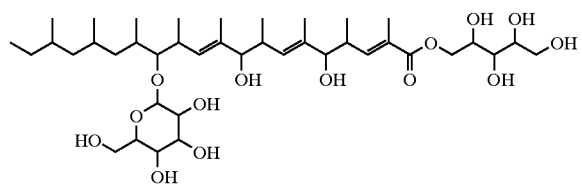

and stereoisomers KF-1040T5A and KF-1040T5B which are compounds represented by the following formula [II],

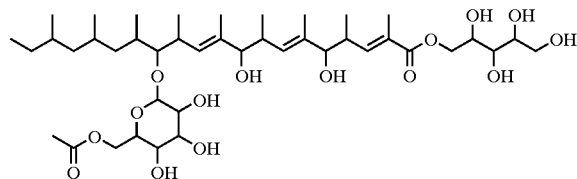

is cultivated in a culture medium to accumulate KF-1040T4A and/or KF-1040T4B and/or KF-1040T5A and/or KF-1040T5B in the culture medium, and the substance KF-1040T4A and/or KF-1040T4B and/or KF-1040T5A and/or KF-1040T5B are harvested from the culture medium. The obtained substances are useful for the prevention and treatment of the diseases relating to arteriosclerosis, obesity, thrombosis, inflammations and immunofunctional disorders.

3 Claims, 16 Drawing Sheets

SUBSTANCES KF-1040T4A, KF-1040T4B, KF-1040T5A, AND KF-1040T5B, AND PROCESS FOR PRODUCING SAME

BACKGROUND OF THE INVENTION

1. Field of the Invention

The present invention relates to novel substances KF-1040T4A, KF-1040T4B, KF-1040T5A and KF-1040T5B having an inhibitory activity for lipid metabolism, and a process for producing such substances.

2. Description of Related Art

There are known anti-obesity drugs and drugs for hyperlipemia. For example, a centrally acting anorectic, Majindol (A. J. Stunkard and J. Rush, Ann. Intern. Med., 81, 526–533, 1974) reduces the biosynthesis of lipids by suppressing appetite, which may, however, be harmful for health in some cases owing to the reduction of appetite. Therefore, it has been desired to develop a new anti-obesity drug or a therapeutic drug for hyperlipemia which has no such side effect.

On the other hand, it has recently became clear that the hydrolysis of sphingomyelin, which is one of lipids constituting mammalian plasmamembrane, is involved in the intracellular signal transduction by cytokine, such as interleukin 1β or tumor necrosis factor ⁻α [Y A. Hannun, J. Biol. Chem., 269, 3125–3128 (1994) and R. Kolesnick & D. W. Golde, Cell, 77, 325–328 (1994)], in the intracellular signal transduction upon activation of T cells [L. M. Boucher et al., J. Exp. Med., 18, 2059–2068 (1995); A. Ochi, Medicinal Immunol., 28, 397–401 (1994)], in diseases such as arteriosclerosis, thrombosis, inflammations and so on, and in the immunoregulation mechanisms.

However, any prophylactic or therapeutic medicament for these diseases has not yet been developed in practice from a drug which specifically and strongly inhibits sphingomyelinase, a hydrolase of sphingomyelin.

In recent years, with the improvement of diet, there has been an increase of life-style related diseases, especially obesity and hyperlipemia caused by the accumulation of triacylglycerols. These diseases have caused serious problems in the therapeutic and preventive medical sciences as the cause or potentiation of various diseases. Diseases which tend to accompany obesity and hyperlipemia caused by the accumulation of triacylglycerols include arteriosclerosis, fatty liver, hypertension, diabetes, and so on. Currently, the population of the patients with these diseases is increasing.

Obesity refers to a physical state in which the stored fat, constituted mainly of triacylglycerols, is accumulated excessively in the body, and is ascribed to an increased synthesis of triacylgyceroles causing extraneous accumulation of fat in the adipocytes. Also, triacylglycerolaemia is believed to be triggered by facilitation of triacylglycerol synthesis in the intestines and the liver, which causes a lipoproteineamia with a high concentration of triacylglycerols in the blood.

Therefore, it is assumed that any substance exhibiting an inhibitory action on diacylglycerol acyltransferase which involves the selective synthesis of triacylglycerols may have the ability to suppress the accumulation of triacylglycerols and may be effective for these diseases.

Under the circumstances, it is worthwhile in the therapy of obesity and hyperlipemia and of various adult diseases such as arteriosclerosis and so on, originating therefrom, to provide a substance having an activity of inhibiting diacylglycerol acyltransferase.

Furthermore, it is also expected that a substance having an activity of inhibiting sphingomyelinase which causes hydrolysis of sphingomyelin, a plasmamembrane constituting lipid, may be useful as an antiarteriosclerotic agent, an antithrombotic agent, an anti-inflammatory agent, and an immunosuppressor, based on a novel function not found heretofore.

SUMMARY OF THE INVENTION

The inventors have conducted various studies for metabolic products produced by microorganisms and found that substances which have activities for inhibiting diacylglycerol acyltransferase and sphingomyelinase are produced in the culture medium during the cultivation of a fungal strain KF-1040 newly separated from a sea weed. These active substances capable of inhibiting the metabolism of lipids have been then isolated from the culture medium and purified, wherefrom substances having the chemical structures represented by the formulae [I], and [II] described below have been found. Since the substances having the chemical structures have not been known heretofore, the inventors have named them substances KF-1040T4A, KF-1040T4B, KF-1040T5A and KF-1040T5B.

The present invention has been accomplished based on such findings and it relates to the stereoisomers KF-1040T4A and KF-1040T4B comprising the compound represented by the following formula [I],

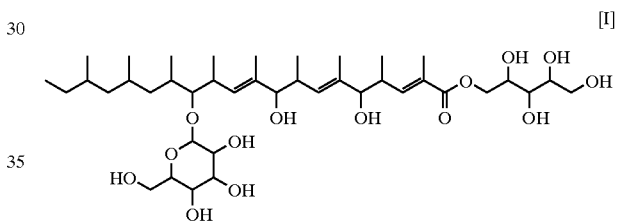

and the stereoisomers KF-1040T5A and KF-1040T5B represented by the following formula [II],

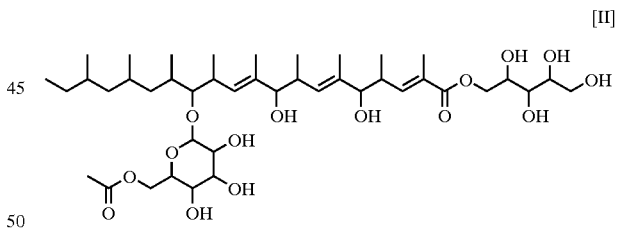

The present invention further relates to a process for producing novel substances KF-1040T4A, KF-1040T4B, KF-1040T5A and KF-1040T5B comprising the steps of culturing a microorganism which belongs to the genus Gliocladium and has the ability to produce substance KF-1040T4A and/or KF-1040T4B and/or KF-1040T5A and/or KF-1040T5B in a culture medium, causing to accumulate the substance KF-1040T4A and/or KF-1040T4B and/or KF-1040T5A and/or KF-1040T5B in the culture medium, and harvesting the substance KF-1040T4A and/or KF-1040T4B and/or KF-1040T5A and/or KF-1040T5B from the culture medium.

The present invention also relates to a process for producing the substances KF-1040T4A, KF-1040T4B, KF-1040T5A and KF-1040T5B, wherein a microorganism which belongs to the genus Gliocladium and has the ability to produce substance KF-1040T4A and/or KF-1040T4B and/or KF-1040T5A and/or KF-1040T5B is Gliocladium sp. KF-1040 (FERM BP-6251).

The present invention further relates to a microorganism which belongs to the genus Gliocladium and has the ability to produce substance KF-1040T4A and/or KF-1040T4B and/or KF-1040T5A and/or KF-1040T5B. The microorganism having the ability to producing the substances KF-1040T4A, KF-1040T4B, KF-1040T5A and KF-1040T5B represented by the formulae [I] and [II] (hereinafter referred to as "substance KF-1040 producing fungus") belongs to the genus Gliocladium and, for example, the fungal strain Gliocladium sp. KF-1040 isolated by the inventors is an example to be utilized most effectively in the present invention. The myocological properties of the present strain KF-1040 are as described below.

DETAILED DESCRIPTION OF THE INVENTION

1. Morphological Properties

Figure 1:
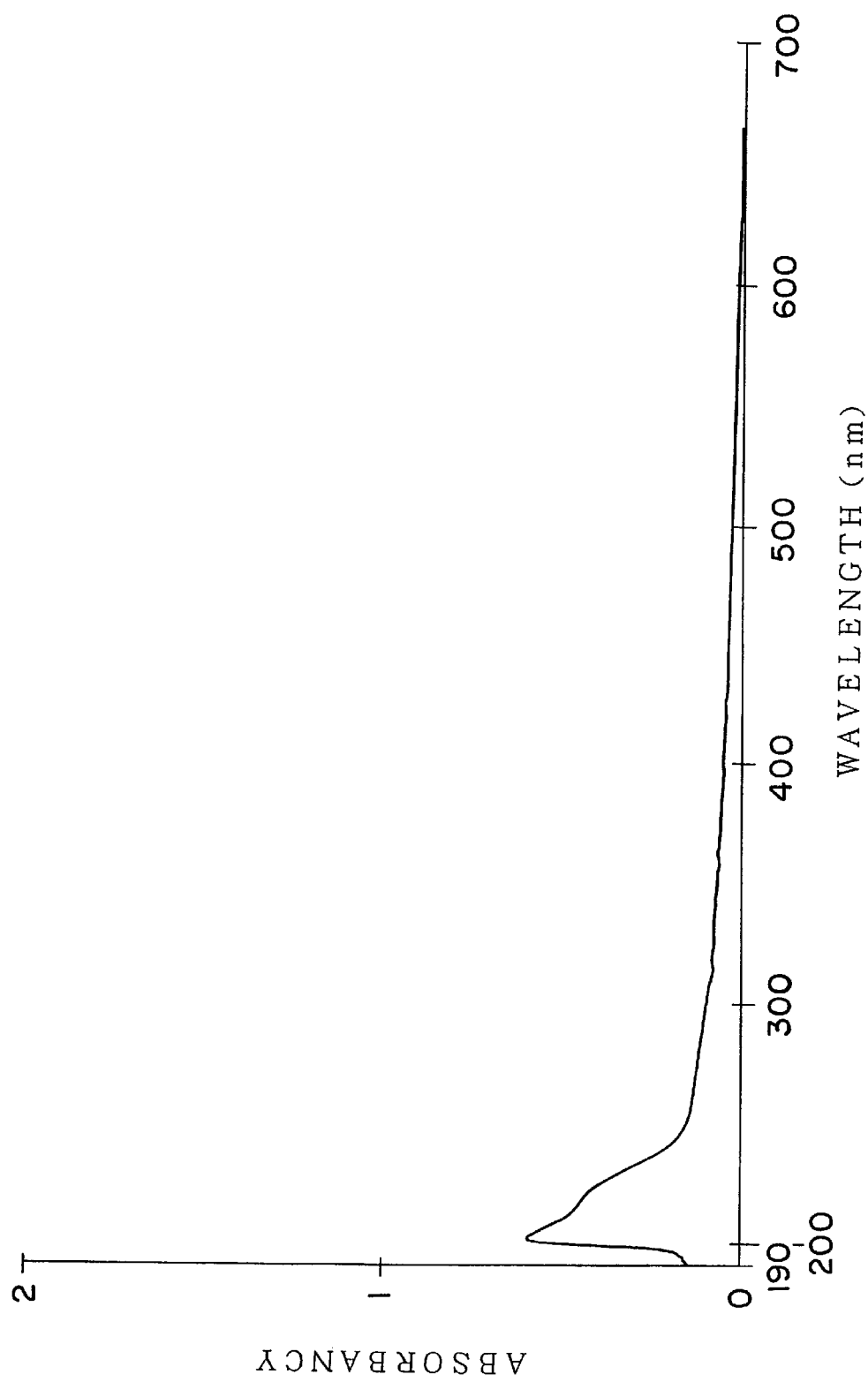
FIG. 1 shows the UV absorption spectrum (in methanol) of the substance KF-1040T4A of the present invention.

The present strain grows relatively well in media, such as potato glucose agar, cornmeal agar, malt extract agar medium, Miura agar medium or seawater starch agar containing 50% of seawater (salt concentration of 3.4%), with abundance of conidia.

On microscopic observation of a colony grown on a cornmeal agar medium, the hypha is transparent and has a septum. The conidiophore assumes both penicillate and verticillate forms. The penicillate conidiophore (having a length of 100 to 200 μm) erects or branches from the basal hypha and forms at the top end or at the branch several penicillate cyclic phialides of sizes of 2.5 to 3.0 μm×10 to 23 μm, on which a conidial mass is formed.

On the other hand, the verticillate conidiophore (having a length of 25 to 50 μm) erects from the basal hypha and forms at the top end or at the branch phialides (of sizes of 3.0 to 5.0 μm×17 to 25 μm) in the form of an elongate flask or of a cone converging toward the top, from which a sole conidial mass is formed. The conidium is colorless and has the shape of an ellipsoid or elongate ellipsoid of a size of 2.5 to 3.0 μm×3.0 to 5.0 μm, rarely with sharp tip at its one end, for the penicillate conidiophore. For the verticillate, the conidium is colorless and has an ellipsodial or elongate ellipsodial form of a size 2.5 to 3.0 μm×6.0 to 8.5 μm.

2. Cultural Properties on Various Agar Media

The results of visual observation of the state of culture of this strain in various culture media at 25° C. for 14 days were as described in the following Table 1. In these culture media, sclerotia or sclerotium-like structures are not formed.

TABLE 1

| Medium Growth condition on medium (Diam. of colony) | Color of surface of colony | Color of reverse surface surface of colony | Soluble pigment |
|---|---|---|---|
| Potato-glucose agar medium | | | |
| good (28–30 mm) floccose, flat | bright gray | bright gray | none |
| Cornmeal agar medium | | | |
| good (24–30 mm) floccose, stripped | bright gray | bright gray | none |
| Malt extract agar medium | | | |
| good (20–22 mm) floccose, flat | pale gray | bright gray | none |
| Miura agar medium | | | |
| good (22–24 mm) floccose, slightly wrinkled | bright gray | bright gray | none |
| Seawater starch agar medium | | | |
| good (24–27 mm) floccose, flat | bright gray | white milky | none |

3. Physiological Properties (1) Optimum Growth Conditions

Optimum growth conditions of the present strain are: pH 4 to 8, temperature 17 to 27° C., * seawater concentration 0 to 50%.

*: natural seawater having a salt concentration of 3.4% is used.

(2) Growth Range

Growth range of the strain is: pH 3 to 10, temperature 9 to 32° C., * seawater concentration 0 to 200%.

*: natural seawater having a salt concentration of 3.4% is used.

(3) Discrimination of Aerobic or Anaerobic: Aerobic

As shown in the above, based on the morphological properties, culturing properties and physiological properties of the present strain KF-1040, the comparison of this strain with known fungal strains was carried out, resulting in the identification thereof as a strain belonging to the genus Gliocladium and named Gliocladium sp. KF-1040.

The present strain was deposited on Feb. 6, 1998, at National Institute of Bioscience and Human-Technology, Agency of Industrial Science and Technology. Ministry of International Trade and Industry, Japan, under the deposition No. FERM P-16629, and was then re-deposited on Feb. 12, 1998, at International Patent Organism Depositary National Institute of Advanced Industrial Science and Technology located at AIST Tsukuba Central 6, 1-1, Higashi 1-Chome Tsukuba-shi, Ibaraki-ken 305-8566 Japan, under the deposit No. FERM BP-6251 from the original deposition by the request for transfer to a deposition based on the Budapest Treaty.

As the substance KF-1040 producing fungus to be employed according to the present invention, the above strain Gliocladium sp. KF-1040 is mentioned, but as a general rule in fungi, the mycological properties have a marked tendency to mutate and are not constant. Therefore, every strain which belongs to the genus Gliocladium and produces the substances KF-1040T4A, KF-1040T4B, KF-1040T5A and KF-1040T5B represented by the formulae [I] and [II] described above including artificial mutants resulting from irradiation of UV ray and X-ray carried out naturally or in a usual manner and by mutational treatment with, for example N-methyl-N'-nitro-N-nitrosoguanidine or 2-aminopurine, fused strains and gene-manipulated strains, are considered to be strains within the scope of the present invention.

For the production of the substances KF-1040T4A, KF-1040T4B, KF-1040T5A and KF-1040T5B, the substance KF-1040 producing fungus belonging to the genus Gliocladium is cultured in a culture medium. As the nutrient sources suitable for the substance KF-1040 producing fungus, nutrient media containing carbon sources assimilable by the microorganism, nitrogen sources digestible by the microorganism and, if necessary, inorganic salts, vitamins, and the like are employed.

As the above assimilable carbon source, saccharides, such as glucose, fructose, maltose, lactose, galactose, dextrin and starch, and vegetable oils, such as soybean oil, may be incorporated alone or in combination. As the digestible nitrogen source, there may be employed peptone, yeast extract, meat extract, soybean powder, cotton seed powder, corn steep liquor, malt extract, casein, amino acids, urea, ammonium salts and nitrates either alone or in combination. Further, if necessary, salts such as phosphates, magnesium salts, calcium salts, sodium salts and potassium salts as well as heavy metal salts such as iron salts, manganese salts, copper salts, cobalt salts and zinc salts, and vitamins and other materials suitable for the production of the present substances may be added.

During culture, an antifoaming agent, such as liquid paraffin, an animal oil, a vegetable oil, a silicone or a surfactant, may be added if necessary, if severe foaming occurs. The cultivation may favorably be carried out usually in a liquid culture medium, while both liquid and solid media can be employed so long as the above nutrient sources are contained. In a small scale production, a culture in a flask may be suitable. For producing the objective material industrially on a large scale, an aerating culture with agitation is preferable, as in other fermentation processes.

In case the culture is carried out in a large tank, it is preferable to proceed in such a manner that the producing fungus is first inoculated in a relatively small amount of culture medium to cultivate therein, in order to obviate delay of growth of the fungus, and the culture mixture is then transferred to the large tank to effect the production culture therein. In that case, it is possible that the culture medium compositions for the pre-culture and for the production culture are the same as or different from each other. If necessary, both the culture compositions may be altered.

In case the culture is carried out under aeration with agitation, known techniques including mechanical agitation by propeller or other means, rotation or shaking of the fermenter, pumping agitation and air bubbling may be suitably employed. Air for the aeration is used after sterilization thereof.

The culture temperature may suitably be altered within the range in which the present substance KF-1040 producing fungus can produce the substances KF-1040T4A, KF-1040T4B, KF-1040T5A and KF-1040T5B. Usually, cultivation is carried out at a temperature of 20 to 30° C., preferably around 27° C. The cultivation is performed usually at a pH of 5 to 8, preferably around 7. The duration of cultivation may vary according to each specific culture condition, but is usually from 10 to 20 days.

The substances KF-1040T4A, KF-1040T4B, KF-1040T5A and KF-1040T5B produced in this manner are present in the thus-grown mycelia and in the cultured filtrate. For separating the desired substances KF-1040T4A, KF-1040T4B, KF-1040T5A and KF-1040T5B from the cultured mass, the entire cultured mass is extracted with a water-missible organic solvent, such as acetone, and the extract is subjected to evaporation under a reduced pressure to remove the organic solvent, whereupon the resulting residue is extracted with a water-immissible organic solvent, such as ethyl acetate.

In addition to the above-mentioned extraction technique, known practices employed for purifying lipid-soluble substances, such as for example, adsorption chromatography, gel filtration chromatography, thin layer chromatography, centrifugal countercurrent partition chromatography, or high performance liquid chromatography, may be employed in a suitable combination or with repetition to effect separation of the substances KF-1040T4A, KF-1040T4B, KF-1040T5A and KF-1040T5B into each component and to purify them.

The physico-chemical properties of the substances KF-1040T4A, KF-1040T4B, KF-1040T5A and KF-1040T5B of the present invention are as follows.

Figure 2:
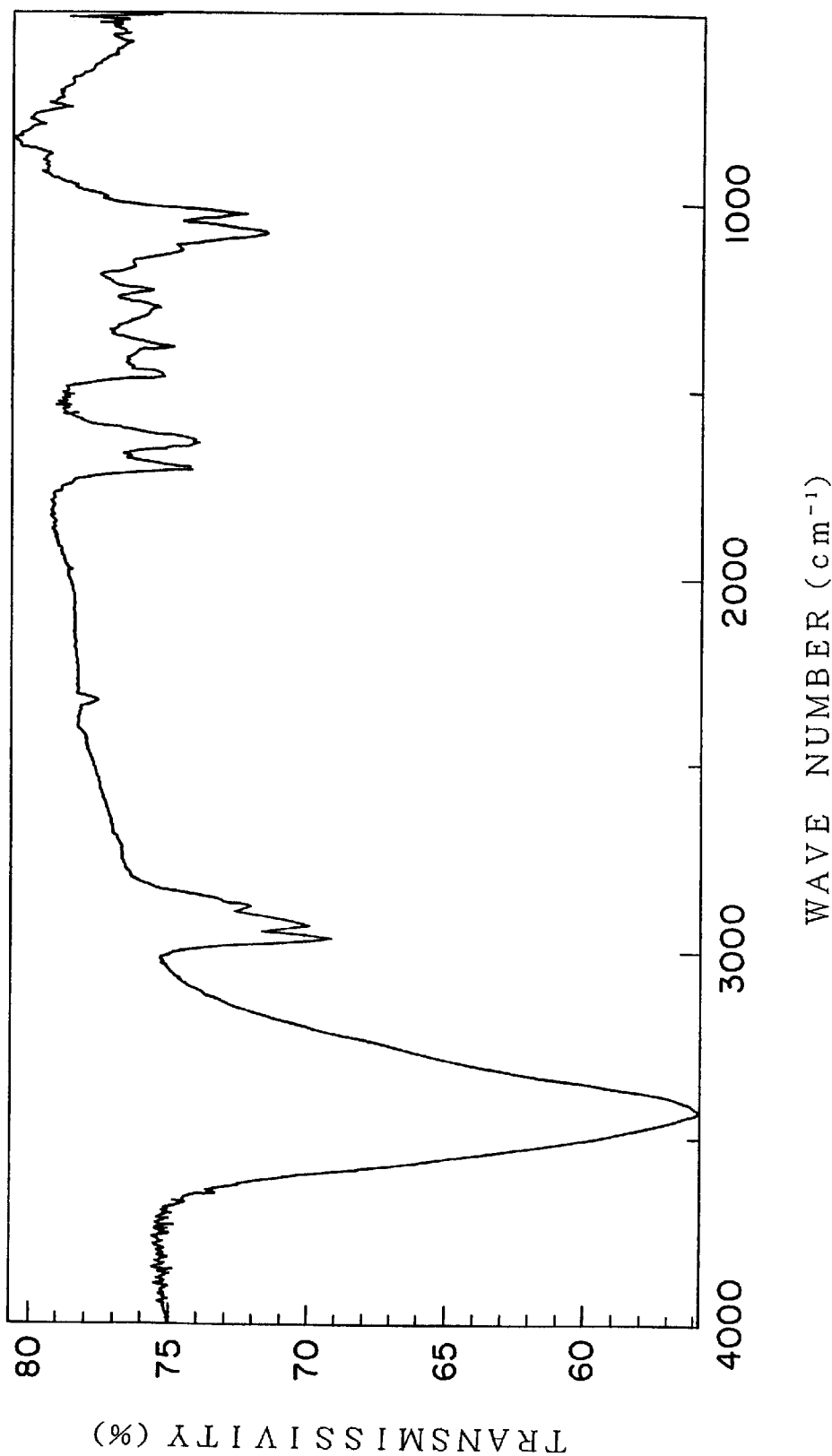
FIG. 2 shows the IR absorption spectrum (with KBr) of the substance KF-1040T4A of the present invention.
Figure 3:
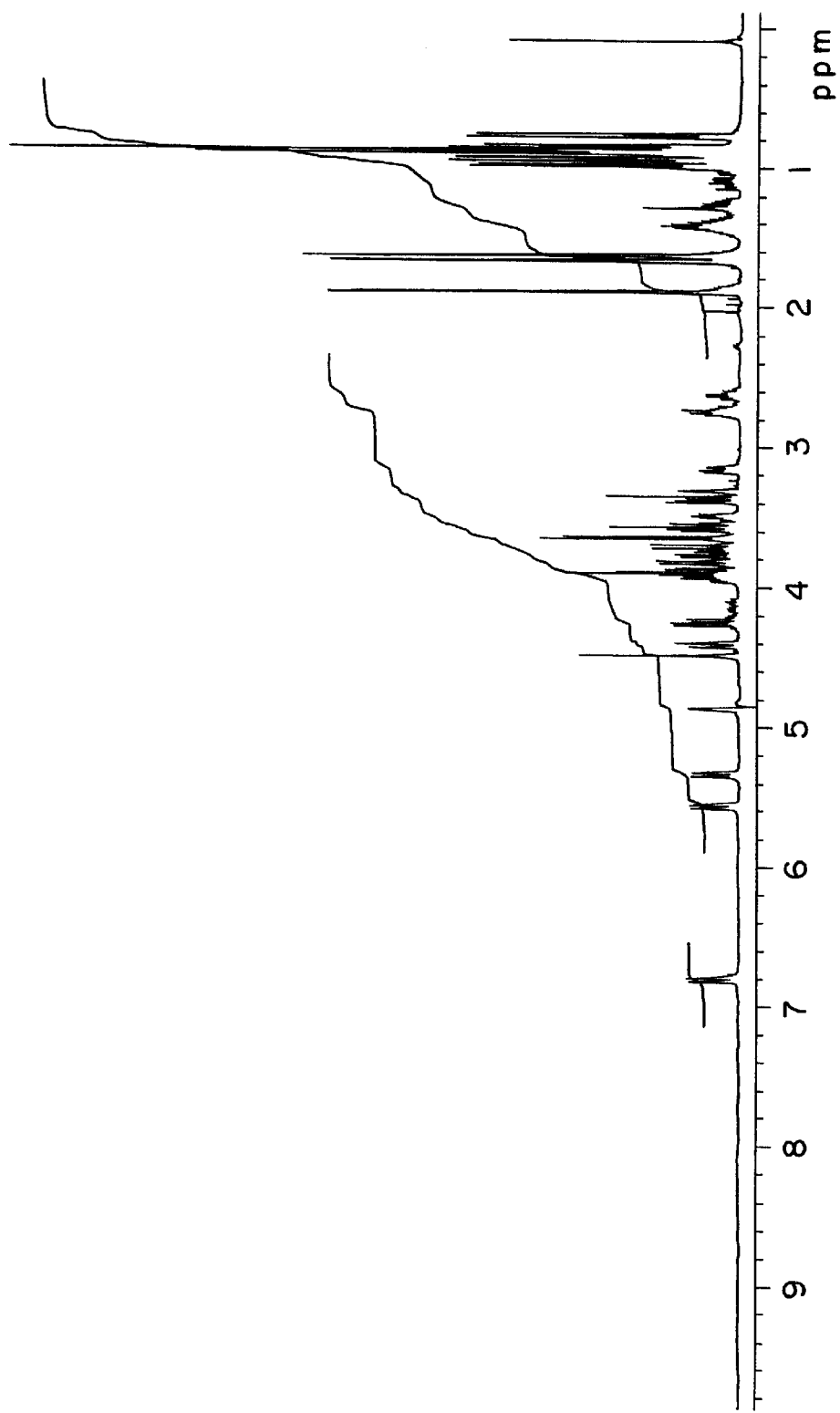
FIG. 3 shows the proton NMR spectrum (in heavy methanol) of the substance KF-1040T4A of the present invention.
Figure 4:
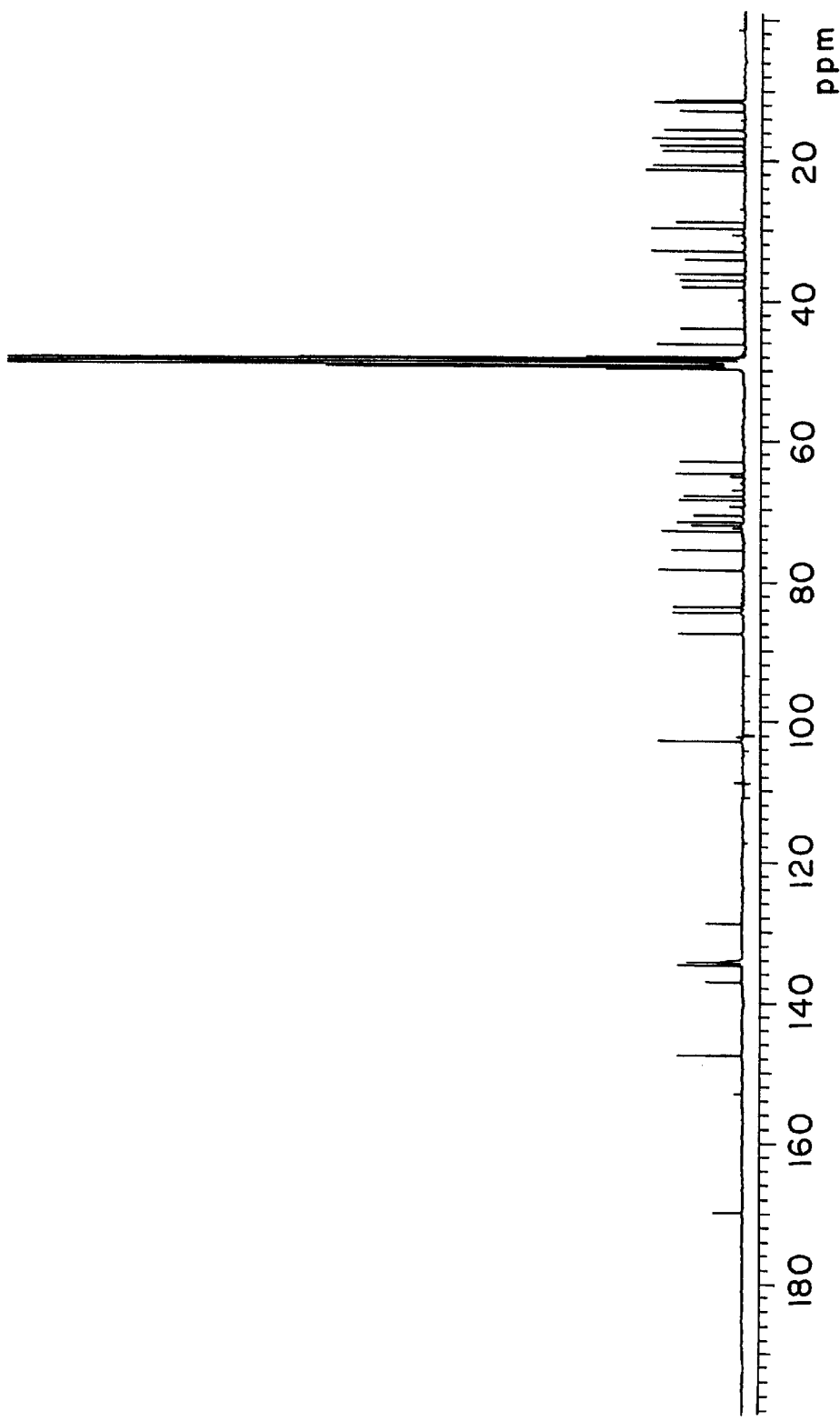
FIG. 4 shows the $^{13}$C-NMR spectrum (in heavy methanol) of the substance KF-1040T4A of the present invention.

[I] Substance KF-1040T4A
(1) Nature: white powder
(2) Molecular weight: 776 (by fast atom bombardment mass spectrometry)
(3) Molecular formula: $C_{40}H_{72}O_{14}$
(4) Specific rotation: $[\alpha]_D^{24}=+12°$ (c=0.1, methanol)
(5) Melting point: 36.7° C.
(6) UV absorption spectrum: UV absorption spectrum measured in methanol is as shown in FIG. 1, and it shows characteristic absorption maxima at around 203 nm ($\epsilon$=45800) and 222 nm ($\epsilon$=33100)
(7) IR absorption spectrum: IR absorption spectrum measured by KBr tablet method is as shown in FIG. 2, and it has characteristic absorption maxima at 3437, 2962, 2927, 2875, 1707, 1641, 1630, 1458, 1375, 1275, 1228, 1074 and, 1026 $cm^{-1}$.
(8) Proton NMR spectrum: Proton NMR spectrum measured on a NMR spectrometer (manufactured by Varian Japan Co.) in heavy methanol is shown in FIG. 3.
(9) $^{13}$C-NMR spectrum: $^{13}$C-NMR spectrum measured on a NMR spectrometer (manufactured by Varian Japan Co.) in heavy methanol is shown in FIG. 4.

(10) Solubility in solvents: soluble in methanol, benzene, chloroform and ethyl acetate; slightly soluble in water and hexane

(11) Color reaction: positive to sulfuric acid and to phosphomolybdic acid

(12) Acidic, neutral, or alkaline discrimination: neutral substance

As a result of precise examination of the various physicochemical properties and spectral analyses data of the substance KF-1040T4A of the present invention as given above, the substance KF-1040T4A of the present invention was determined to have the chemical structure represented by the following formula [I]:

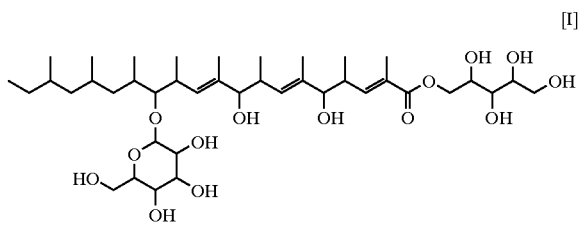

[I]

[II] Substance KF-1040T4B (1) Nature: white powder (2) Molecular weight: 776 (by fast atom bombardment mass spectrometry)

(3) Molecular formula: $C_{40}H_{72}O_{14}$ (4) Specific rotation: $[\alpha]_D^{24}=+8°$ (c=0.1, methanol)

(5) Melting point: 35.6° C.

Figure 5:
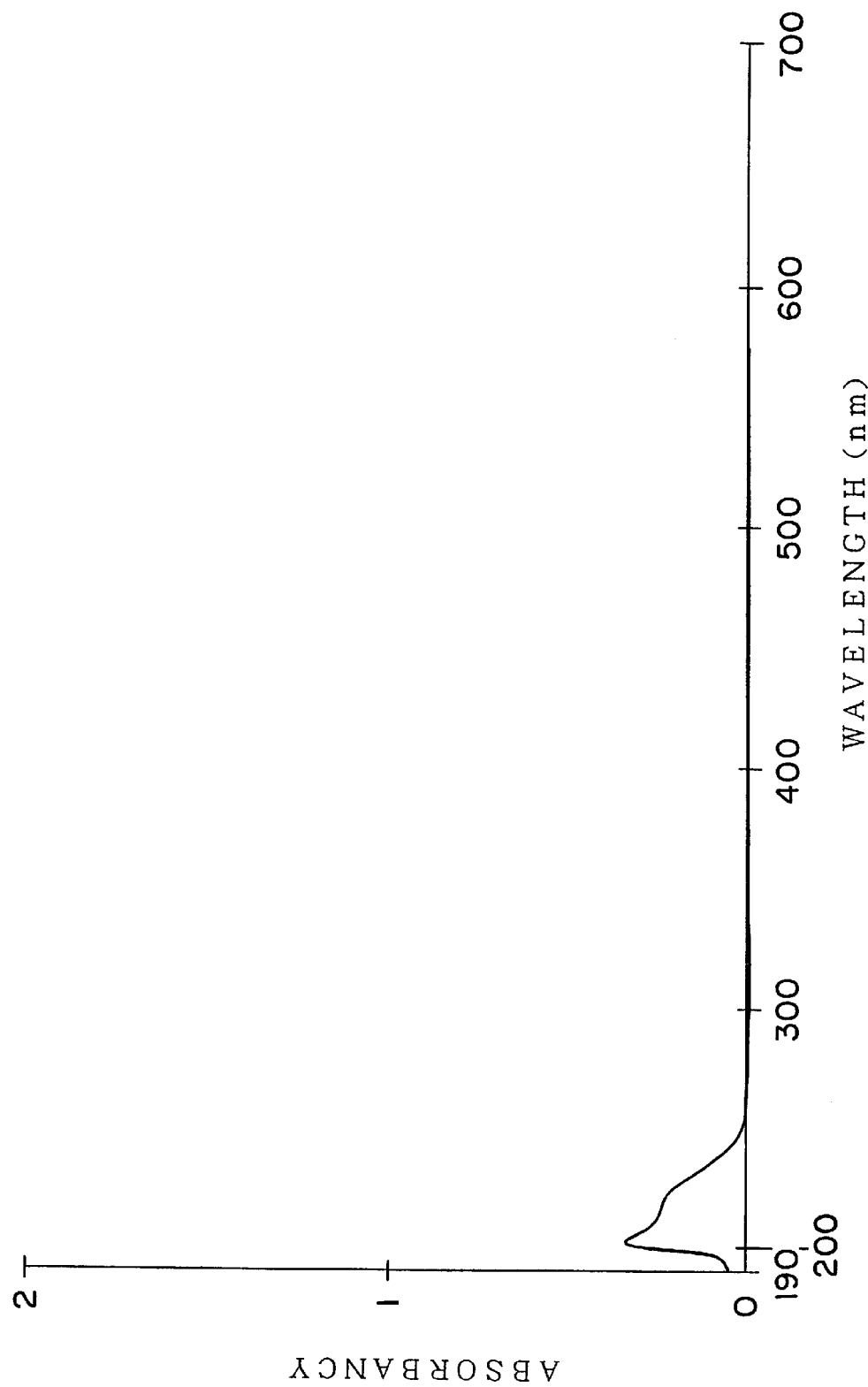
FIG. 5 shows the UV absorption spectrum (in methanol) of the substance KF-1040T4B of the present invention.

(6) UV absorption spectrum: UV absorption spectrum measured in methanol is as shown in FIG. 5, and it shows characteristic absorption maxima at around 203 nm ($\epsilon=25800$) and 222 nm ($\epsilon=17800$)

Figure 6:
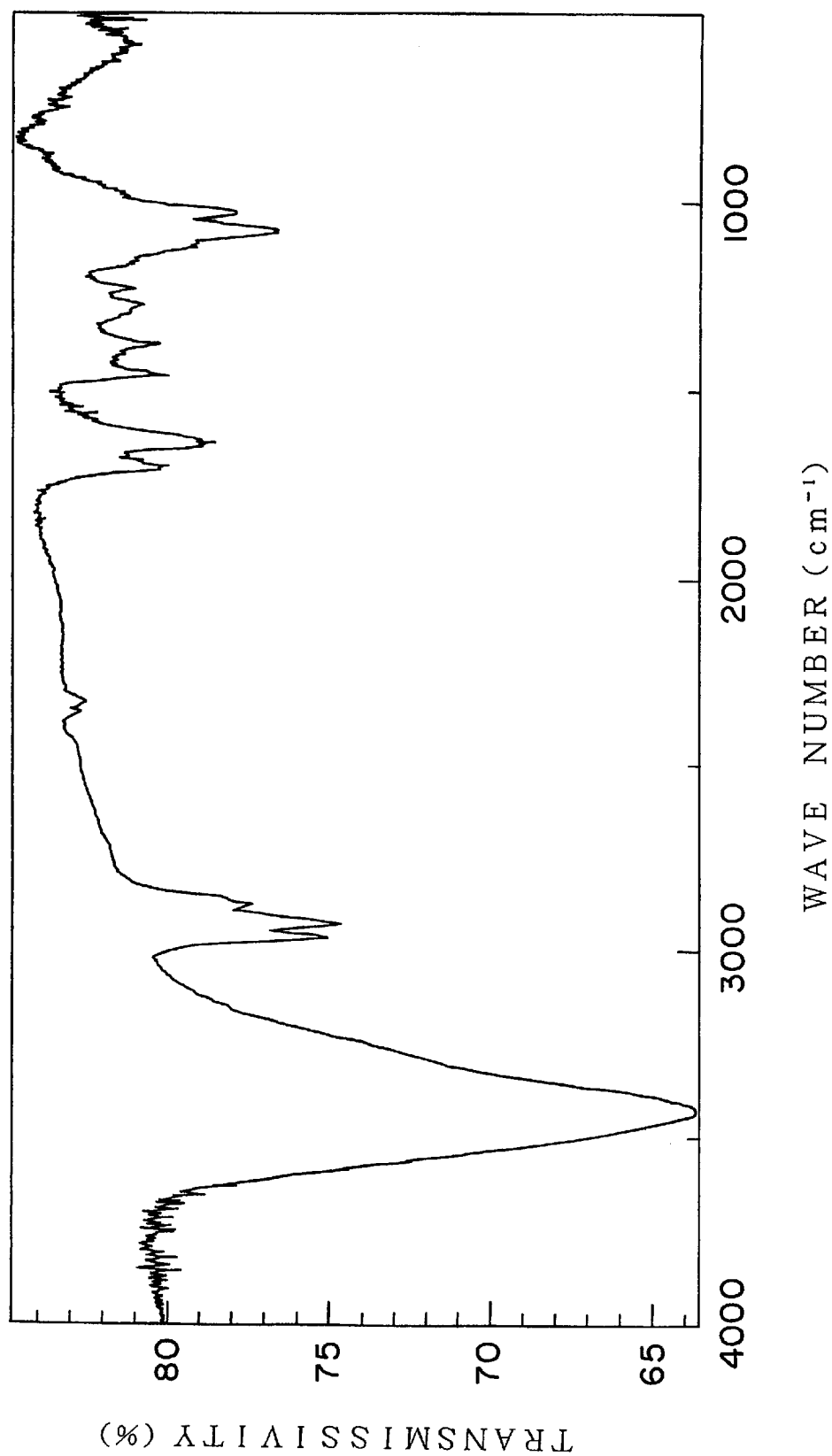
FIG. 6 shows the IR absorption spectrum (with KBr) of the substance KF-1040T4B of the present invention.
Figure 7:
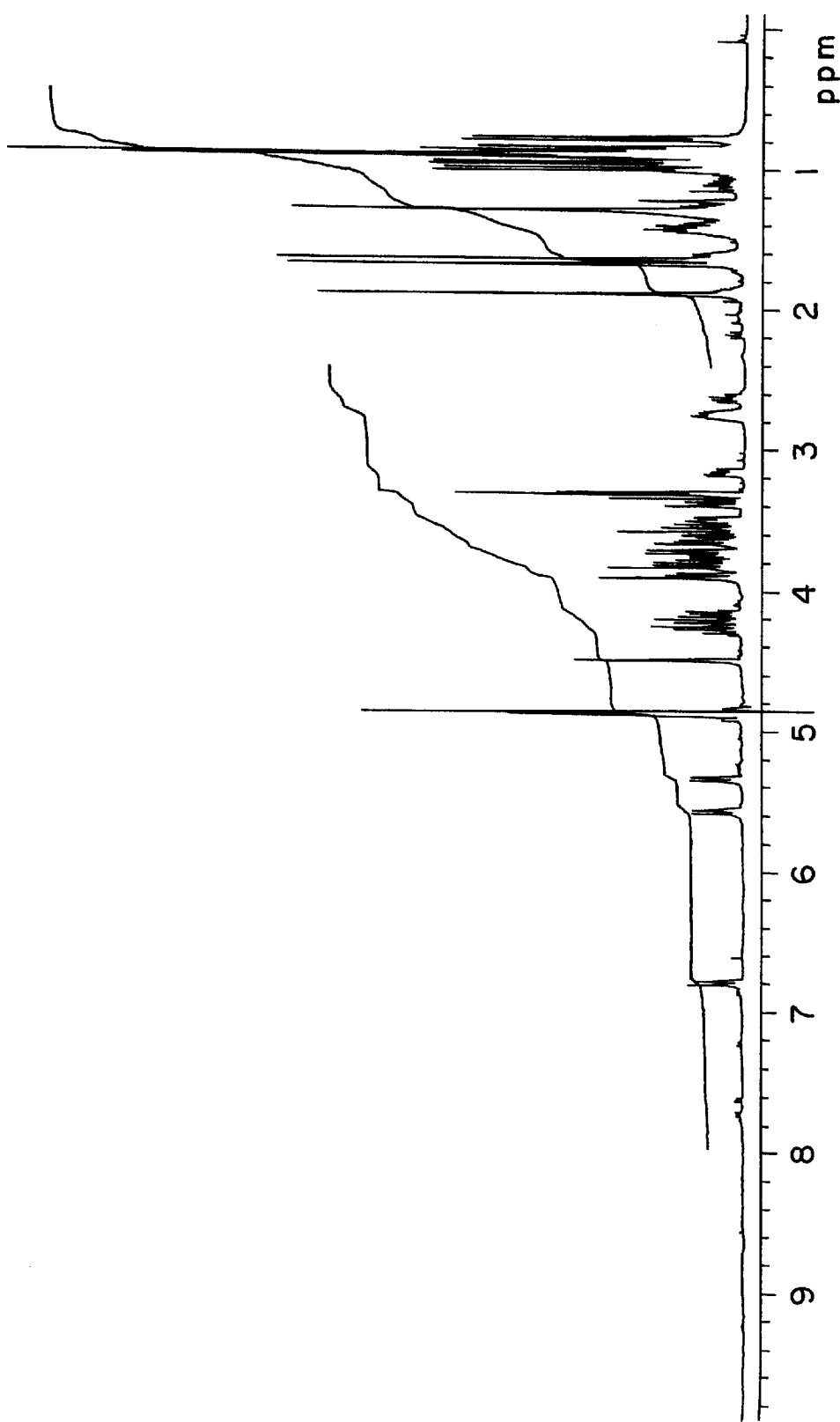
FIG. 7 shows the proton NMR spectrum (in heavy methanol) of the substance KF-1040T4B of the present invention.

(7) IR absorption spectrum: IR absorption spectrum measured by KBr tablet method is as shown in FIG. 6, and it has characteristic absorption maxima at 3437, 2960, 2926, 2873, 2854, 1701, 1653, 1637, 1458, 1375, 1269, 1230, 1070 and, 1024 $cm^{-1}$ (8) Proton NMR spectrum: Proton NMR spectrum measured on a NMR spectrometer (manufactured by Varian Japan Co.) in heavy methanol is shown in FIG. 7.

Figure 8:
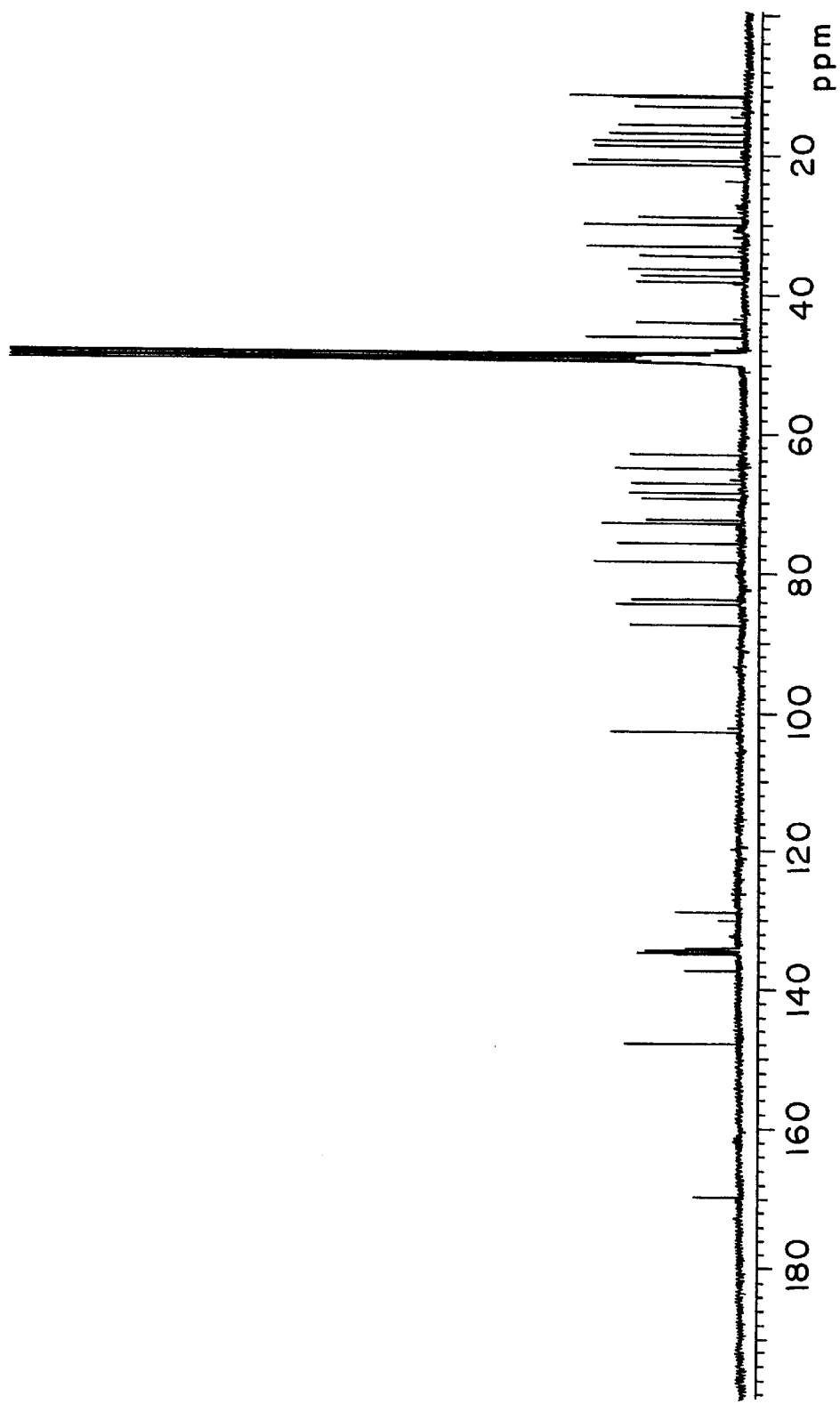
FIG. 8 shows the $^{13}$C-NMR spectrum (in heavy methanol) of the substance KF-1040T4B of the present invention.

(9) $^{13}$C-NMR spectrum: $^{13}$C-NMR spectrum measured on a NMR spectrometer (manufactured by Varian Japan Co.) in heavy methanol is shown in FIG. 8.

(10) Solubility in solvents: soluble in methanol, benzene, chloroform and ethyl acetate; slightly soluble in water and hexane

(11) Color reaction: positive to sulfuric acid and to phosphomolybdic acid

(12) Acidic, neutral, or alkaline discrimination: neutral substance

As a result of precise examination of the various physicochemical properties and spectral analyses data of the substance KF-1040T4B of the present invention as given above, the substance KF-1040T4B of the present invention was determined to have the chemical structure represented by the following formula [I]:

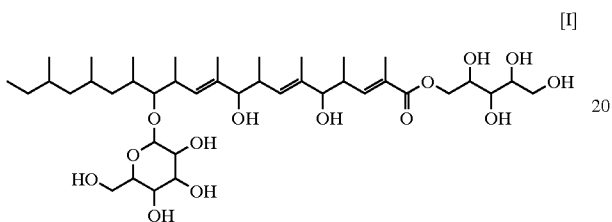

[I]

[III] Substance KF-1040T5A (1) Nature: colorless oil (2) Molecular weight: 818 (by fast atom bombardment mass spectrometry)

(3) Molecular formula: $C_{42}H_{74}O_{15}$ (4) Specific rotation: $[\alpha]_D^{24}=+22°$ (c=0.1, methanol)

Figure 9:
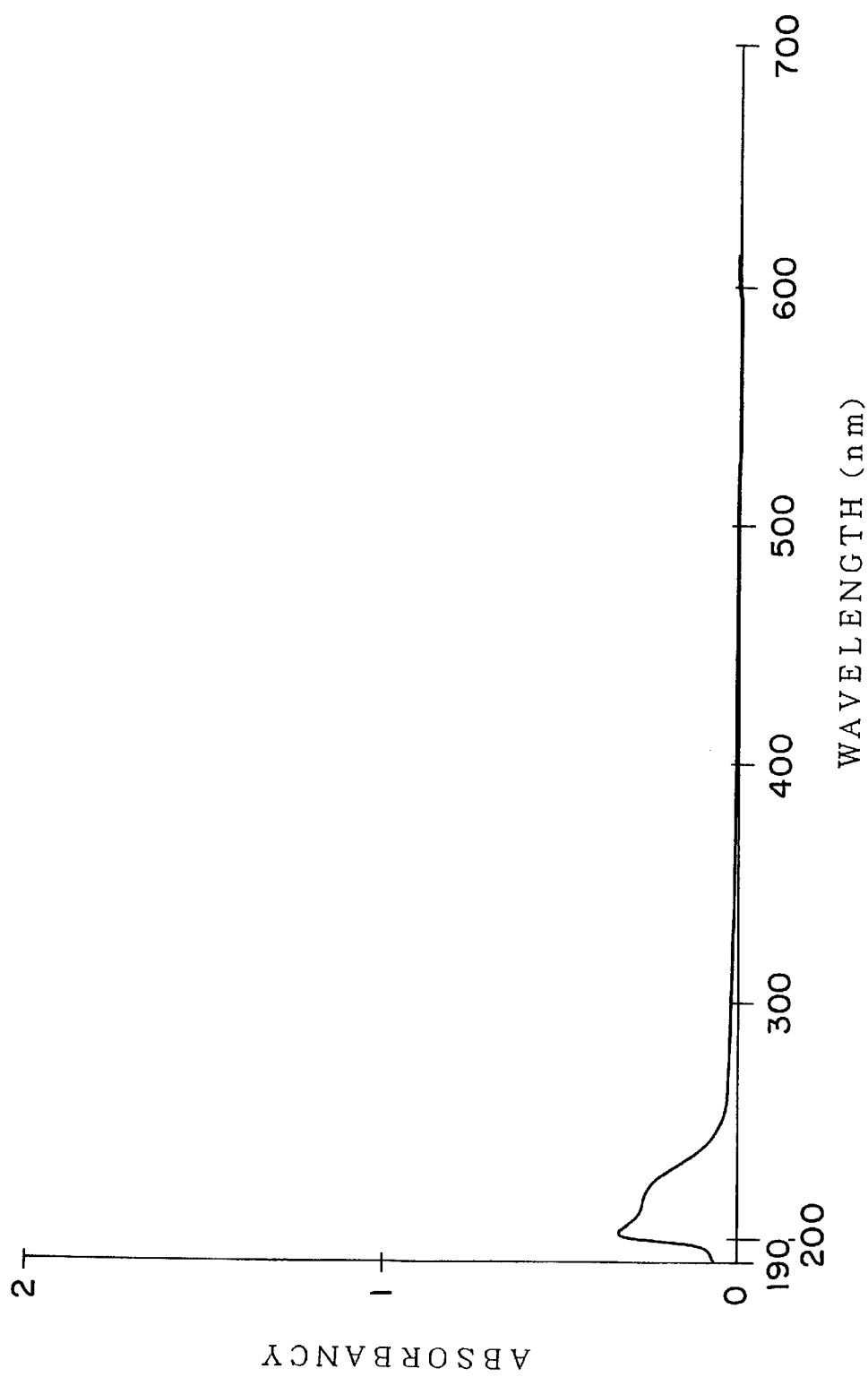
FIG. 9 shows the UV absorption spectrum (in methanol) of the substance KF-1040T5A of the present invention.
Figure 10:
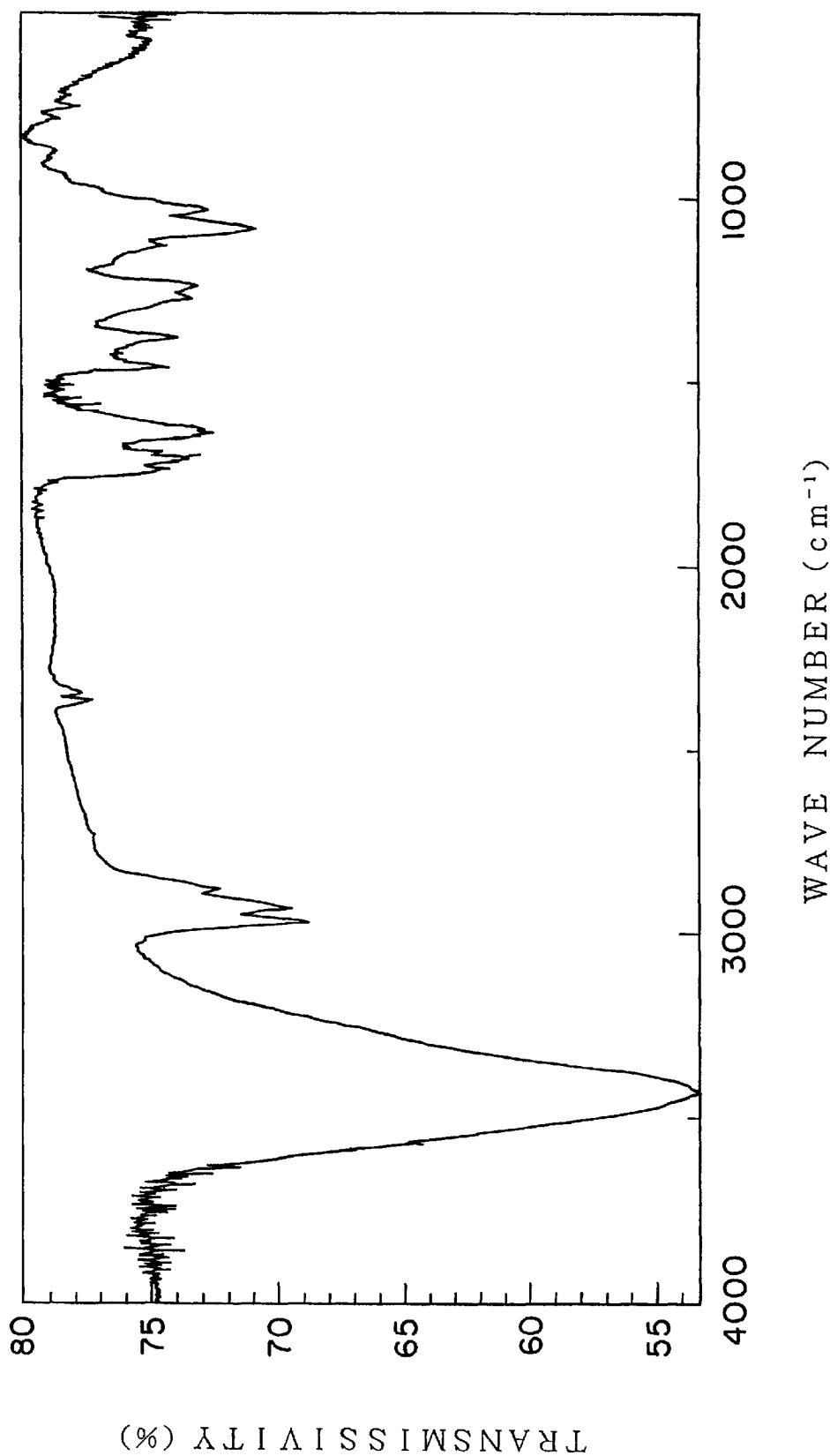
FIG. 10 shows the IR absorption spectrum (with KBr) of the substance KF-1040T5A of the present invention.

(5) UV absorption spectrum: UV absorption spectrum measured in methanol is as shown in FIG. 9, and it shows characteristic absorption maxima at around 203 nm ($\epsilon=27000$) and 222 nm ($\epsilon=20900$)

Figure 11:
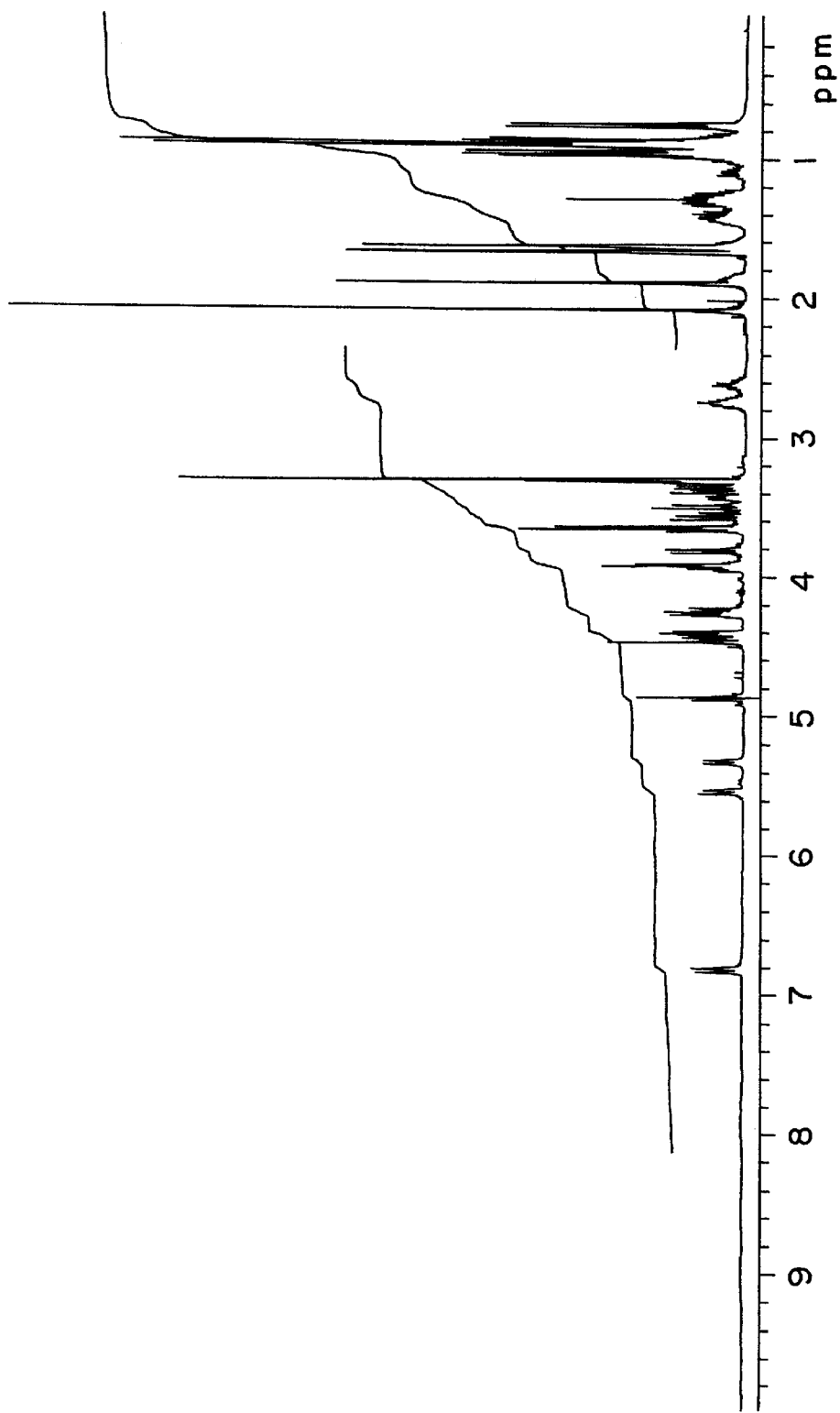
FIG. 11 shows the proton NMR spectrum (in heavy methanol) of the substance KF-1040T5A of the present invention.

(6) IR absorption spectrum: IR absorption spectrum measured by KBr tablet method is as shown in FIG. 2, and it has characteristic absorption maxima at 3434, 2962, 2927, 2873, 1741, 1701, 1655, 1637, 1458, 1375, 1273, 1232, 1128, 1078 and, 1036 $cm^{-1}$ (7) Proton NMR spectrum: Proton NMR spectrum measured on a NMR spectrometer (manufactured by Varian Japan Co.) in heavy methanol is shown in FIG. 11.

Figure 12:
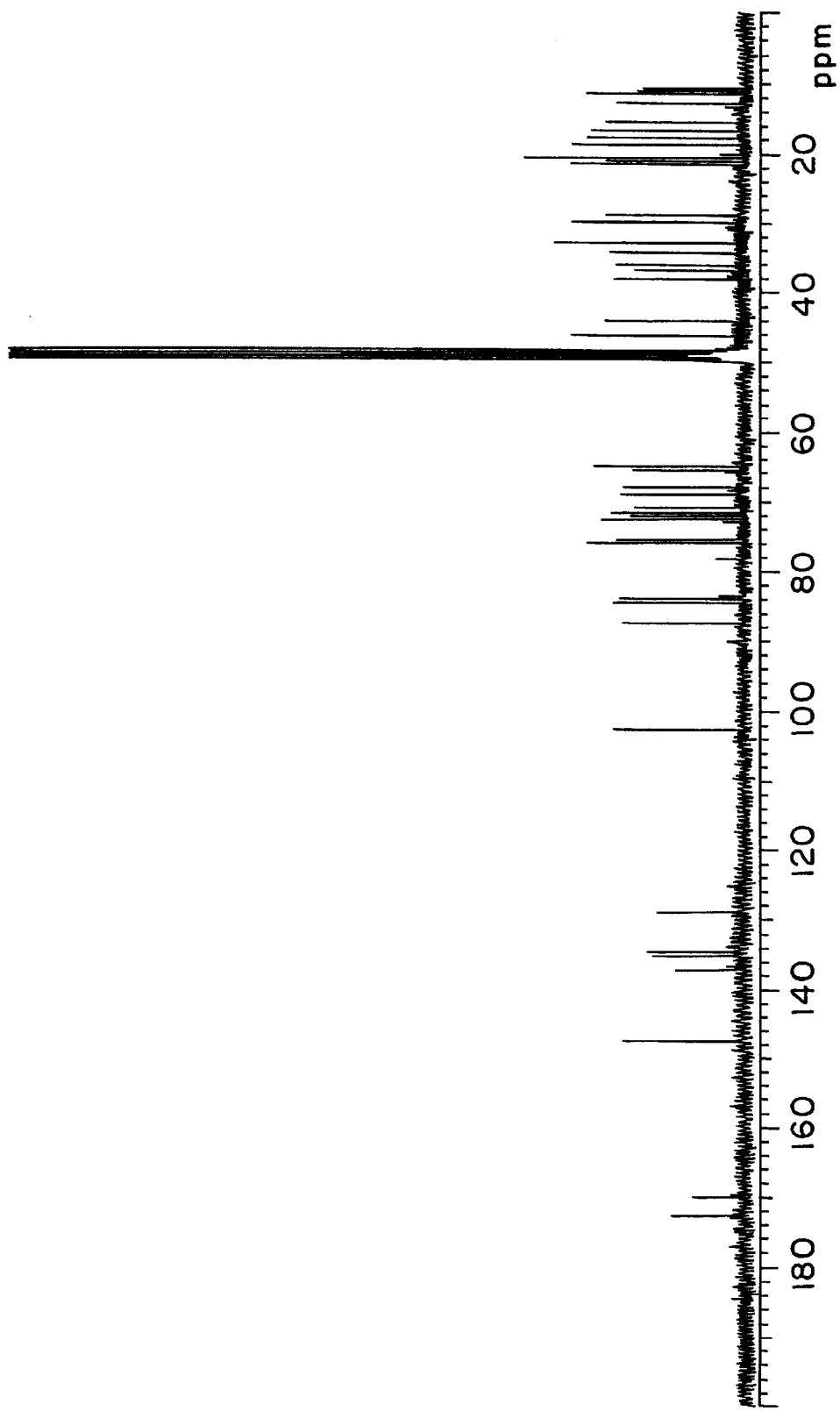
FIG. 12 shows the $^{13}$C-NMR spectrum (in heavy methanol) of the substance KF-1040T5A of the present invention.

(8) $^{13}$C-NMR spectrum: $^{13}$C-NMR spectrum measured on a NMR spectrometer (manufactured by Varian Japan Co.) in heavy methanol is shown in FIG. 12.

(9) Solubility in solvents: soluble in methanol, benzene, chloroform and ethyl acetate; slightly soluble in water and hexane

(10) Color reaction: positive to sulfuric acid and to phosphomolybdic acid

(11) Acidic, neutral, or alkaline discrimination: neutral substance

As a result of precise examination of the various physicochemical properties and analyses spectral data of the substance KF-1040T5A of the present invention as given above, the substance KF-1040T5A of the present invention was determined to have the chemical structure represented by the following formula [II]:

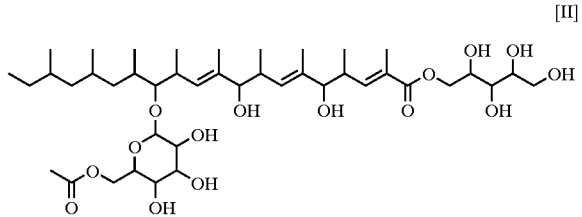

[II]

[IV] Substance KF-1040T5B (1) Nature: colorless oil (2) Molecular weight: 818 (by fast atom bombardment mass spectrometry)

(3) Molecular formula: $C_{42}H_{74}O_{15}$ (4) Specific rotation: $[\alpha]_D^{24}=+10°$ (c=0.1, methanol)

Figure 13:
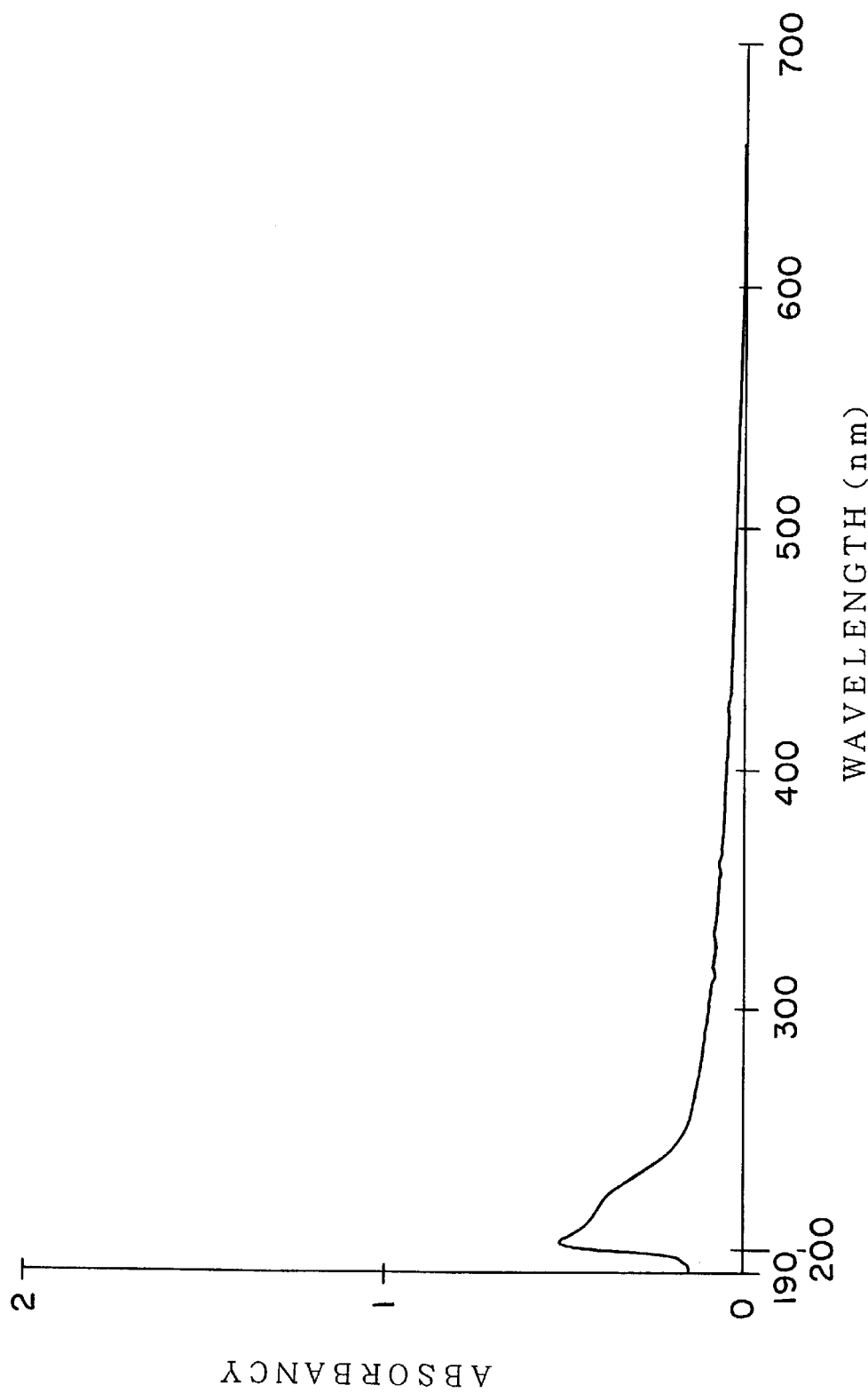
FIG. 13 shows the UV absorption spectrum (in methanol) of the substance KF-1040T5B of the present invention.

(5) UV absorption spectrum: UV absorption spectrum measured in methanol is as shown in FIG. 13, and it shows characteristic absorption maxima at around 203 nm ($\epsilon=41600$) and 222 nm ($\epsilon=32000$)

Figure 14:
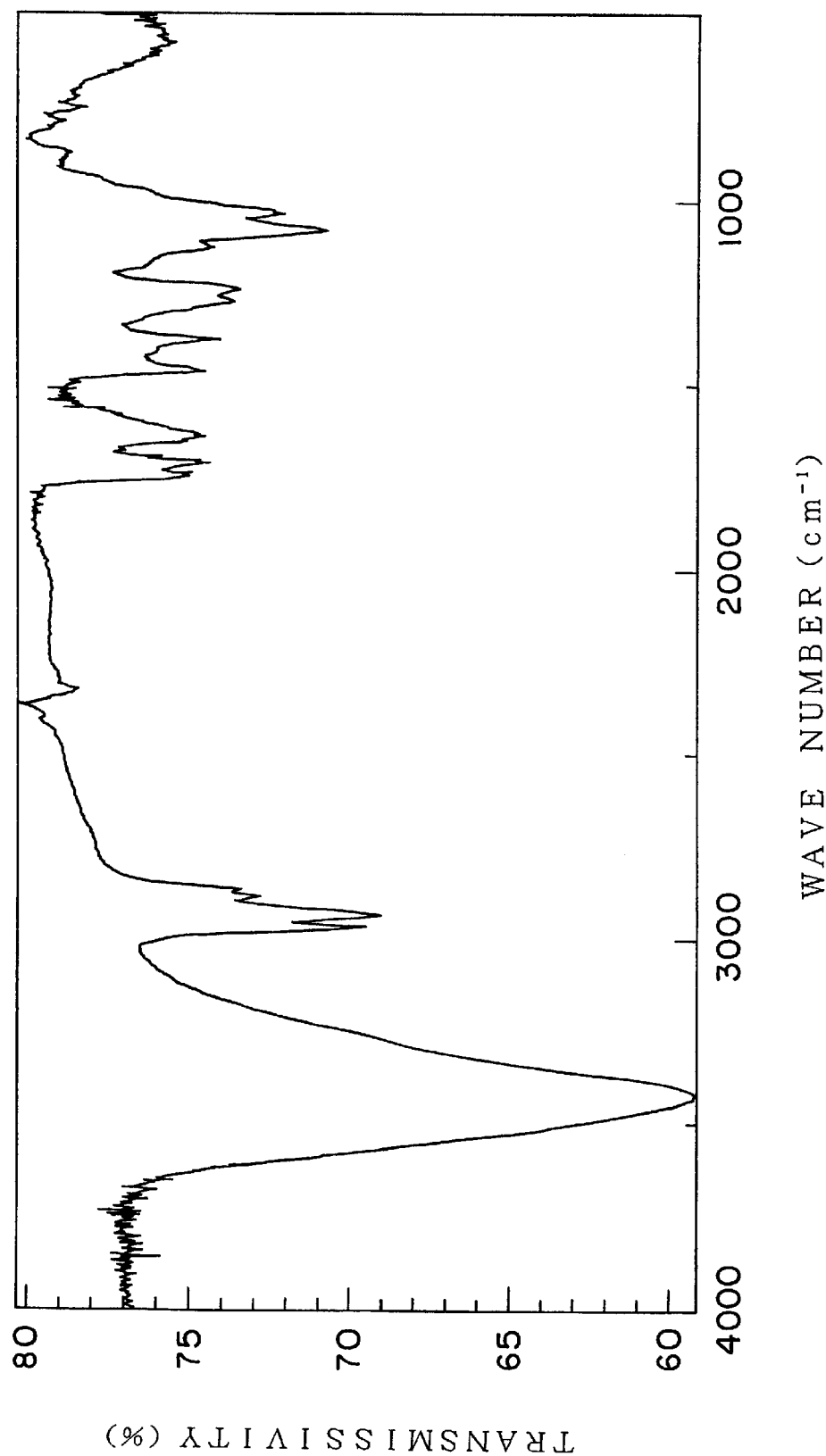
FIG. 14 shows the IR absorption spectrum (with KBr) of the substance KF-1040T5B of the present invention.

(6) IR absorption spectrum: IR absorption spectrum measured by KBr tablet method is as shown in FIG. 14, and it has characteristic absorption maxima at 3434, 2960, 2926, 2873, 2854, 1743, 1707, 1655, 1637, 1458, 1375, 1269, 1238, 1124, 1078 and, 1034 cm$^{-1}$.

Figure 15:
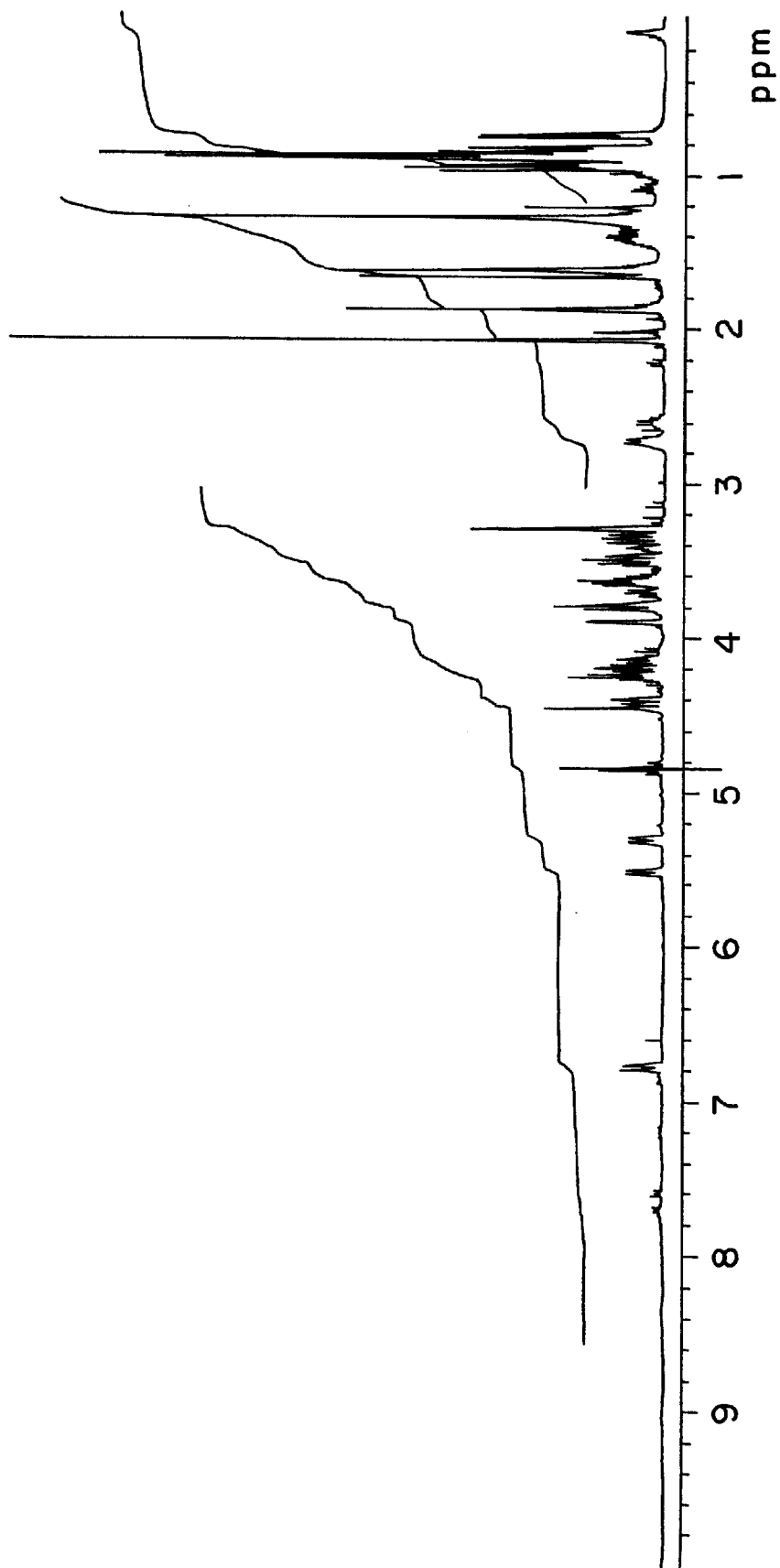
FIG. 15 shows the proton NMR spectrum (in heavy methanol) of the substance KF-1040T5B of the present invention.

(7) Proton NMR spectrum: Proton NMR spectrum measured on a NMR spectrometer (manufactured by Varian Japan Co.) in heavy methanol is shown in FIG. 15.

Figure 16:
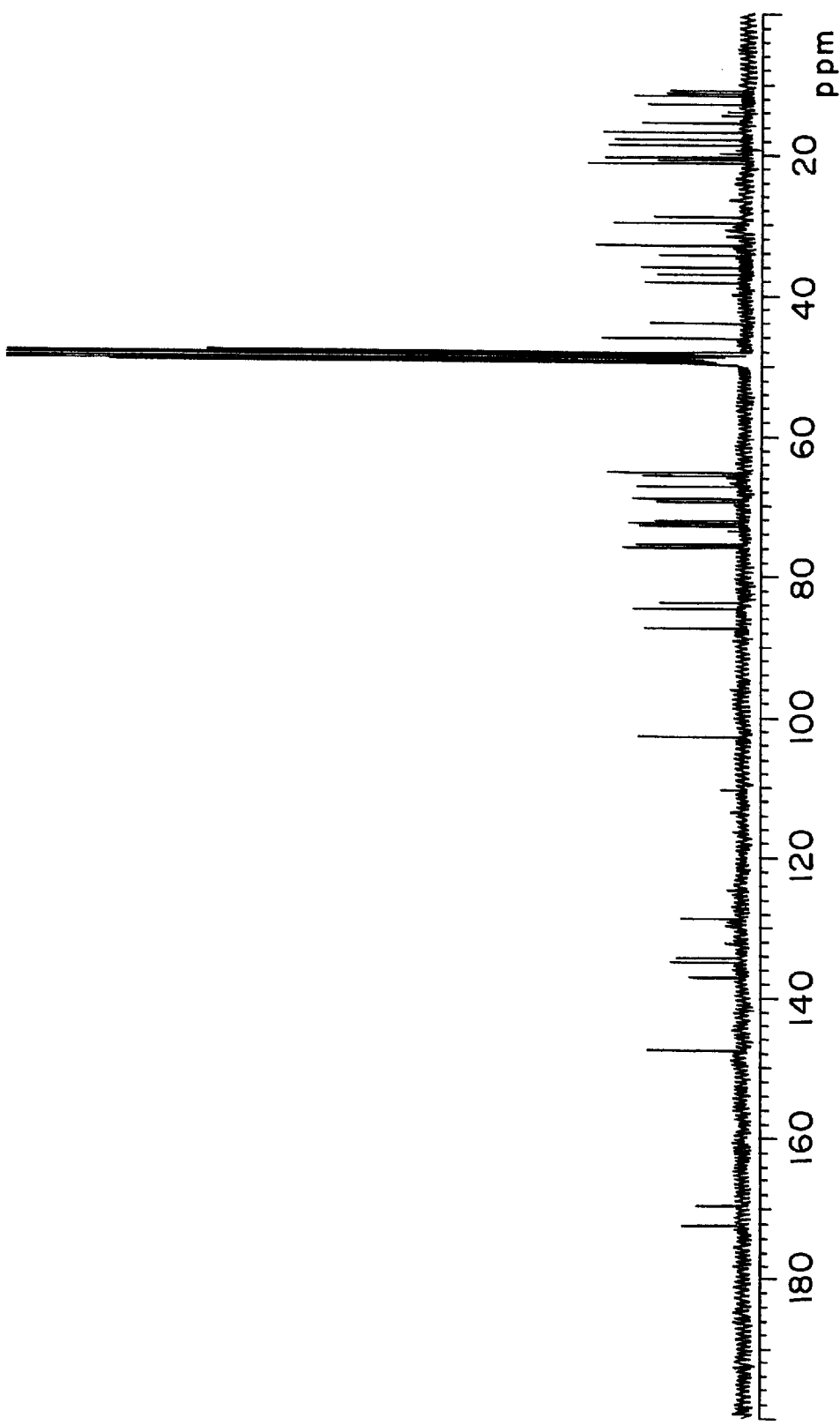
FIG. 16 shows the $^{13}$C-NMR spectrum (in heavy methanol) of the substance KF-1040T5B of the present invention.

(8) $^{13}$C-NMR spectrum: $^{13}$C-NMR spectrum measured on a NMR spectrometer (manufactured by Varian Japan Co.) in heavy methanol is shown in FIG. 16.

(9) Solubility in solvent: soluble in methanol, benzene, chloroform and ethyl acetate; slightly soluble in water and hexane

(10) Color reaction: positive to sulfuric acid and to phosphomolybdic acid

(11) Acidic, neutral, or alkaline discrimination: neutral substance

As a result of precise examination of the various physicochemical properties and spectral analyses data of the substance KF-1040T5B of the present invention as given above, the substance KF-1040T5B of the present invention was determined to have the chemical structure represented by the following formula [II]:

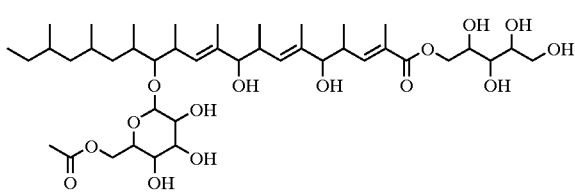

[II]

While the description in the above has been directed to the details of various physico-chemical properties of the substances KF-1040T4A, KF-1040T4B, KF-1040T5A and KF-1040T5B, it is to be recognized that any compound having properties consistent with each of these properties has not been reported in the literature. Therefore, it has been determined that the substances KF-1040T4A, KF-1040T4B, KF-1040T5A and KF-1040T5B are novel substances.

The following is a description of the biological nature of the substances KF-1040T4A, KF-1040T4B, KF-1040T5A and KF-1040T5B.

(1) Inhibitory Action against Rat-originated Diacylglycerol Acyltransferase

The activity of diacylglycerol acyltransferase was determined in accordance with the method of Mayorek and BarTana, [J. Biol. Chem., 260, 6528–6532 (1985)] with partial modification.

Namely, a microsomal fraction prepared from rat liver was used as the enzyme source. To a 175 mM Tris-HCl buffer (pH 8.0) containing 8 mM of MgCl$_2$, 1 mg/ml of bovine serum albumin and 2.5 mM of diisopropyl fluorophosphate, there were added 0.75 mM of dioleoylglycerol and 30 μM of [1$^{-14}$C] palmitoyl-CoA (0.02 μCi) and the total volume was adjusted to 200 μl, whereupon the enzymatic reaction mixture was incubated at 23° C. for 15 minutes. The total lipids were extracted with chloroform/methanol (1/2) mixture and each lipid was separated by a TLC (with Kiselgel GF$_{254}$ and a developing solvent of petroleum ether/diethyl ether/acetic acid of 80/20/1), followed by measurement of the radioactivity of the triacylglycerol fraction using RI RADIO-SCANNER (manufactured by AMBIS System Inc., U.S.A.) to determine the diacylglycerol acyltransferase activity.

The calculation of the drug concentration corresponding to 50% inhibition of this enzyme gives the values of 13.2 μg/ml for the substance KF-1040T4A, 11.6 μg/ml for the substance KF-1040T4B, 18.0 μg/ml for the substance KF-1040T5A, and 14.7 μg/ml for the substance KF-1040T5B.

(2) Inhibitory Action against Synthesis of Triacylglycerol in Human-originated Cells (Raji Cell originating from Human Burkitt Lymphoma)

The assessment of the influence of the substances on triacylglycerol synthesis was performed in accordance with the method of Tomoda et al. [J. Biol. Chem., 266, 4214–4219 (1991)] using human-originated cells (Raji cell originated from human Burkitt lymphoma). A Raji cell dispersion of 2.7×10$^6$ cells per milliliter containing 0.36 nM [1$^{-14}$C] oleic acid (0.02 μCi) was filled up to a total volume 200 μl, whereupon the reaction proceeded at 37° C. for 30 minutes. The total lipids were extracted with a chloroform/methanol (2/1) mixture. Then, the activity was measured in the same manner as in the "inhibitory action against rat-originated diacylglycerol-acyltransferase".

The calculation of the drug concentration corresponding to 50% inhibition of triacylglycerol synthesis gives a value of 10 μg/ml for all the substances KF-1040T4A, KF-1040T4B, KF-1040T5A and KF-1040T5B.

(3) Inhibitory Action on Rat Brain-originated Neutral Sphingomyelinase

The assessment of influence of the substances on the neutral sphingomyelinase originating from rat brain was performed in accordance with the modified method of Murakami and Arima [J. Neurochem., 52, 611–618 (1989)].

Namely, a membrane fraction prepared from a rat brain was used as the enzyme source and thereto were added 20 mM of HEPES-NaOH buffer solution (pH 7.4), 6.5 mM of MgCl$_2$, 0.1% Triton X-100 and 25 μM [N-methyl-$^3$H] sphingomyelin (0.006 μCi) and the mixture was filled up to a total volume of 50 μl. After reaction at 37° C. for 30 minutes, 200μl of chloroform/methanol mixture (1/2 in volume ratio) was added to the reaction mixture to separate the reaction product [$^3$H] phosphocholine from the starting material [$^3$H] sphingomyelin. The upper layer was taken up into a 50 μl vial. The amount of [$^3$H] phosphocholine was quantitatively determined by a liquid scintillation counter to estimate the neutral sphingomyelinase activity.

The calculation of the concentration of the substances of the present invention corresponding to 50% inhibition of this enzyme gives the values of 391 μg/ml for the substance KF-1040T4A and 341 μg/ml for the substance KF-1040T4B.

(4) Influence on Human Placenta-originated Acid Sphingomyelinase

The assessment of the influence of the substances on human placenta-originated acidic sphingomyelinase was performed in accordance with the method of Jones et al. [Biochem. Journal, 195, 373–382 (1981)] with partial modification.

Thus, an acid sphingomyelinase originating from human placenta (a product of Sigma Co.) was used as the enzyme source and thereto were added 250 mM of sodium acetate buffer solution (pH 5.0), 0.1% of NP-40 (a product of Sigma Co.), and 25 μM [N-methyl-$^3$H] sphingomyelin (0.006 μCi), and the mixture was filled up to a total volume of 50 μl. After reaction at 37° C. for 30 minutes, 200 μl of chloroform/methanol mixture (1/2 in volume ratio) was added thereto to separate the reaction product [$^3$H] phosphocholine from the starting material [$^3$H] sphingomyelin. The upper layer was taken up into a 50 μl vial. The amount of [$^3$H] phosphocholine was quantitatively determined by a liquid scintillation counter to estimate the acid sphingomyelinase activity.

The calculation of the concentration of the substances of the present invention corresponding to 50% inhibition of this enzyme gives the values of 233 μg/ml for the substance KF-1040T4A, 70 μg/ml for the substance KF-1040T4B, 196 μg/ml for the substance KF-1040T5A, and 49 μg/ml for the substance KF-1040T5B.

As described above, the novel substances according to the present invention exhibit the activity on inhibiting diacylglycerol acyltransferase and sphingomyelinase and, hence, are useful for the prevention and treatment of the diseases relating to arterisclerosis, obesity, thrombosis, inflammations and immunofunctional disorder.

BEST-KNOWN MODE FOR CARRYING OUT THE INVENTION

The following will explain the present invention with reference to an example, but the invention is not limited thereto.

Two 500-ml Erlenmeyer flasks charged each with 100 ml of a liquid culture medium (pH 6.0) prepared by dissolving 2.0% of glucose, 0.5% of polypeptone (a product of Nippon Seiyaku K. K.), 0.2% of yeast extract (a product of Oriental Kobo Kogyo K. K.), 0.05% of magnesium sulfate 7 hydrate, 0.1% of potassium dihydrogen phosphate and 0.1% of agar in 50% of natural seawater were inoculated each with one loopful of the strain of Gliocladium sp. KF-1040 (FERM BP-6251), whereupon each inoculated medium was cultured at 27° C. for 4 days with shaking.

The resulting cultured medium was used as the cultured seed, 60 Roux flasks, each of 1000 ml capacity, were charged with 300 ml of a liquid culture medium (pH 6.0) prepared by dissolving 100 g/l of potato and 1.0% of glucose in 50% of natural seawater. After sterilization and cooling, each flask was inoculated aseptically with 3 ml of the culture seed and the inoculated mixture was cultured at 27° C. for 16 days without agitation.

To the total cultured liquor, 18 liters of acetone were added and agitated well, followed by concentration under reduced pressure and the thus-concentrated liquor was again extracted with ethyl acetate. The extract layer was subjected to concentration under a reduced pressure, whereby 2.2 grams of a crude product were obtained. This crude product was dissolved in a small amount of acetonitrile and the resulting solution was passed through an ODS column (200 g, from Senshu Kagaku K. K., ODS-SS-1020T) filled with 30% acetonitrile water. After washing the column with 50% acetonitrile water, the column was eluted with 60% acetonitrile water and then with 70% acetonitrile water. From the eluates, 87 mg of a crude product of the substance T4 and 104 mg of a crude product of the substance T5 were obtained by concentration under reduced pressure.

Each of the crude products was fractionated by a high performance liquid chromatography (YMC-Pack, ODS-AM, 20 mm×250 mm, flow rate=6.0 ml/min.; detection: 220 nm UV using an eluent of 50% acetonitrile water). Fractions eluted at the retention time of 96 minutes and 100 minutes for the substance T4 and fractions eluted at the retention time of 212 minutes and 224 minutes for the substance T5 were collected, respectively. Organic solvent was removed and the aqueous layer was extracted with ethyl acetate to obtain 7.5 mg of the substance KF-1040T4A, 3.3 mg of the substance KF-1040T4B, 2.6 mg of the substance KF-1040T5A, and 4.2 mg of the substance KF-1040T5B.

EEFECT OF THE INVENTION

As pointed out above, the novel substances KF-1040T4A, KF-1040T4B, KF-1040T5A and KF-1040T5B according to the present invention exhibit activity for inhibiting diacylglycerol acyltransferase and sphingomyelinase and, hence, are expected to be useful for the prevention and treatment of the diseases relating to arteriosclerosis, obesity, thromobosis, inflammations and immunofunctional disorders.

We claim:

1. A substance selected from the group consisting of KF-1040T4A, KF-1040T4B, KF-1040T5A and KF-1040T5B, wherein KF-1040T4A and KF-1040T4B are stereoisomers of the compound represented by the following formula [I],

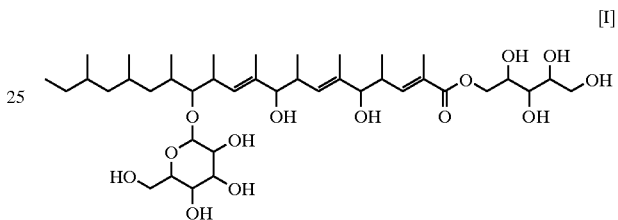

and wherein KF-1040T5A and KF-1040T5B are stereoisomers of the compound represented by the following formula [II],

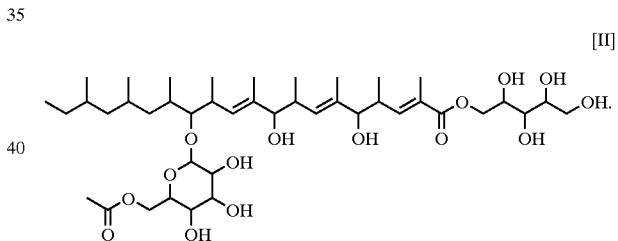

2. A process for producing substances KF-1040T4A, KF-1040T4B, KF-1040T5A and KF-1040T5B, comprising the steps of:

cultivating a microorganism which is Gliocladium KF-1040 (FERM BP-6251) and which produces a substance selected from the group consisting of KF-1040T4A, KF-1040T4B, KF-1040T5A and KF-1040T5B in a culture medium, causing said substance to accumulate in the culture medium, and harvesting said substance from the culture medium.

3. A microorganism which is Gliocladium KF-1040 (FERM BP-6251) and which produces a substance selected from the group consisting of KF-1040T4A, KF-1040T4B, KF-1040T5A and KF-1040T5B.

* * * * *